United States Patent
Xu et al.

(10) Patent No.: US 10,929,420 B2
(45) Date of Patent: Feb. 23, 2021

(54) STRUCTURED REPORT DATA FROM A MEDICAL TEXT REPORT

(71) Applicant: Siemens Healthcare GmbH, Erlangen (DE)

(72) Inventors: Juan Xu, Beijing (CN); Puneet Sharma, Princeton Junction, NJ (US)

(73) Assignee: Siemens Healthcare GmbH, Erlangen (DE)

(*) Notice: Subject to any disclaimer, the term of this patent is extended or adjusted under 35 U.S.C. 154(b) by 105 days.

(21) Appl. No.: 16/382,358

(22) Filed: Apr. 12, 2019

(65) Prior Publication Data

US 2019/0347269 A1 Nov. 14, 2019

(30) Foreign Application Priority Data

May 8, 2018 (EP) .................................. 18171355

(51) Int. Cl.
*G06F 16/25* (2019.01)
*G16H 15/00* (2018.01)
*G06F 16/2452* (2019.01)
*G06F 40/258* (2020.01)
*G06F 40/295* (2020.01)

(52) U.S. Cl.
CPC ...... *G06F 16/258* (2019.01); *G06F 16/24522* (2019.01); *G06F 40/258* (2020.01); *G06F 40/295* (2020.01); *G16H 15/00* (2018.01)

(58) Field of Classification Search
CPC ...... G16H 15/00; G16H 10/60; G06F 16/258; G06F 16/26; G06F 16/3329
USPC .......................................................... 704/9
See application file for complete search history.

(56) References Cited

U.S. PATENT DOCUMENTS

| | | | |
|---|---|---|---|
| 7,668,718 B2* | 2/2010 | Kahn | G10L 15/063 704/270 |
| 9,984,772 B2* | 5/2018 | Liu | G06F 16/3329 |
| 10,181,360 B1* | 1/2019 | Reicher | G16H 10/60 |
| 10,325,020 B2* | 6/2019 | Burke | G16H 10/20 |
| 10,679,345 B2* | 6/2020 | Madani | G16H 70/00 |

(Continued)

OTHER PUBLICATIONS

Cai, Tianrun, et al. "Natural language processing technologies in radiology research and clinical applications." Radiographics 36.1 (2016): 176-191.

(Continued)

*Primary Examiner* — Susan I McFadden (57) ABSTRACT

Structured report data is generated from a medical text report. A medical text report including one or more natural language statements is acquired. A computer implemented text analysis process analyses the medical text report to determine, for each natural language statement, one or more labels for the natural language statement. Structured report data including the determined one or more labels each in association with natural language data from the natural language statement to which the label corresponds is generated. The computer implemented text analysis process includes, for each natural language statement: determining, for each of the one or more words of the natural language statement, and, using word embeddings, a vector representing the word; and determining, based on the determined one or more vectors, and using a text classification model, the one or more labels associated with the natural language statement.

15 Claims, 4 Drawing Sheets

(56) References Cited

U.S. PATENT DOCUMENTS

2019/0237184 A1* 8/2019 Sharma .................. G16H 30/40
2019/0325300 A1* 10/2019 Xu ........................... G06N 3/08
2020/0117712 A1* 4/2020 Xu ......................... G16H 50/20

OTHER PUBLICATIONS

Mikolov, Tomas, et al. "Distributed representations of words and phrases and their compositionality." Advances in neural information processing systems. 2013.
Zulkarnain, Nur Zareen et al.; "An architecture to support ultrasound report generation and standardisation." Proceedings of the 8th International Conference on Health Informatics. International Conference on Health Informatics (HEALTHINF), 2015.
Banerjee, Imon, et al. "Radiology report annotation using intelligent word embeddings: Applied to multi-institutional chest CT cohort." Journal of biomedical informatics 77 (2018): 11-20. ISSN: 1532-0464, 001: 10.1016/J.JBI.2017.11.012.
Extended European Search Report (EESR) dated Nov. 9, 2018 in corresponding European Patent Application No. 18171355.3.

* cited by examiner

STRUCTURED REPORT DATA FROM A MEDICAL TEXT REPORT

RELATED CASE

This application claims the benefit of EP 18171355, filed on May 8, 2018, which is hereby incorporated by reference in its entirety.

TECHNICAL FIELD

The present embodiments relate to structured report data, and more specifically to a generating structured report data from a medical text report, such as a radiology report.

BACKGROUND

Medical text reports, for example radiology reports, are used in the medical field to communicate information between medical professionals. For example, a patient's physician may refer a patient for certain medical imaging, for example Computed Tomography Angiography (CTA). A radiographer then carries out the medical imaging of the patient, and a radiologist then reads or interprets the resulting image to produce a text-based radiology report of their findings. A medical finding may be defined as an observation made of the patient, for example by a doctor, for example as a result of examination, imaging, or other tests of the patient. The radiology report is then provided to the referring physician. The referring physician may then make a diagnosis of a condition of the patient based on the radiology report.

Radiology reports are created in narrative text form, with a radiologist dictating the findings based on visual, qualitative or quantitative image interpretation. Due to the way in which they are created, different radiologists may produce radiology reports in different ways, resulting in heterogeneous report scope content and/or format.

The free-form and/or heterogeneous nature of the radiology reports can make it difficult to obtain the key knowledge contained therein. For example, it can be difficult for the referring physician to make an efficient diagnosis based thereon, and key-information contained therein may be missed, which could in principle lead to misdiagnosis.

A large volume of such medical text reports may be stored in healthcare databases. The free-form and/or heterogeneous nature of the reports can make it difficult and/or inefficient to update, integrate, and or share information across databases. Further, this can make it difficult and/or inefficient (e.g. computationally expensive) to perform further analysis, i.e. computer implemented analysis and/or searching of the information contained within the medical text reports. For example, performing quantitative analysis in specific group of patients, or of a single patient, or for population health analytics, or cross-sectional analysis to identify high-risk patients and/or improve population health insights, based on the free form medical text reports may be difficult and/or inefficient.

It is therefore desirable to provide a method which enables generation of such structured report data in an efficient and accurate manner.

SUMMARY

According to a first aspect, there is provided a method of generating structured report data from a medical text report, the method including: acquiring a medical text report including one or more natural language statements each including one or more words; analysing, using a computer implemented text analysis process, the medical text report to determine, for each natural language statement, one or more labels for the natural language statement; and generating structured report data including the determined one or more labels each in association with natural language data, the natural language data including the natural language statement or data derived from the natural language statement to which the label corresponds; wherein the computer implemented text analysis process includes, for each natural language statement: determining, for each of the one or more words of the natural language statement, and using word embeddings, a vector representing the word; and determining, based on the determined one or more vectors, and using a text classification model, the one or more labels associated with the natural language statement.

Optionally, the method includes storing the generated structured report data in a structured database such that the determined one or more labels are each stored in association with the natural language data to which the label corresponds.

Optionally, the method includes outputting, based on the generated structured report data, a structured report structured such that the determined one or more labels are each presented in association with the natural language data to which the label corresponds.

Optionally, the structured report data is structured such that the one or more labels are in a first level of a hierarchical structure and the corresponding natural language data are in a second level of the hierarchical structure, the second level being lower than the first level in the hierarchical structure.

Optionally, the method includes performing a computer implemented searching process for said natural language data stored in the structured database based at least in part on said labels stored in the structured database.

Optionally, the computer implemented text analysis process includes, for each natural language statement: determining, for each of a plurality of predefined labels, an association parameter indicating a degree to which the natural language statement is associated with the pre-defined label; wherein the determining the one or more labels associated with the natural language statement is based on the determined association parameter.

Optionally, the method includes: determining, using the text classification model, for each natural language statement, one or more classifications of the natural language statement with respect to a medical finding; wherein, for each natural language statement, the natural language data includes the one or more classifications.

Optionally, the acquiring the medical text report includes acquiring a first of the natural language statements of the medical text report when the first natural language statement has been produced and before a second of the natural language statements of the medical text report has been produced.

Optionally, the method includes training the text analysis process.

Optionally, the training includes training the text classification model based on a database of natural language statements of a plurality of further medical text reports, each statement being annotated with a ground-truth corresponding to a said label.

Optionally, the plurality of further medical text reports are structured medical text reports including one or more said labels each in association with a natural language statement to which the label corresponds, and wherein the ground-truth for each natural language statement includes the label.

Optionally, the training includes building a vocabulary and generating word embeddings from a plurality of further medical text reports or the plurality of further medical text reports, and wherein the determined one or more vectors are determined using the generated word-embeddings.

Optionally, the training is implemented using a neural network architecture.

According to a second aspect, there is provided apparatus for generating structured report data from a medical text report, the apparatus being configured to perform the method according the first aspect.

According to a third aspect, there is provided a computer program including instructions stored on a non-transitory computer readable storage medium, the instructions, when executed on a computer, causing the computer to perform the method according to the first aspect.

Further features and advantages will become apparent from the following description of examples, given by way of example only, which is made with reference to the accompanying drawings.

DETAILED DESCRIPTION

Figure 1:
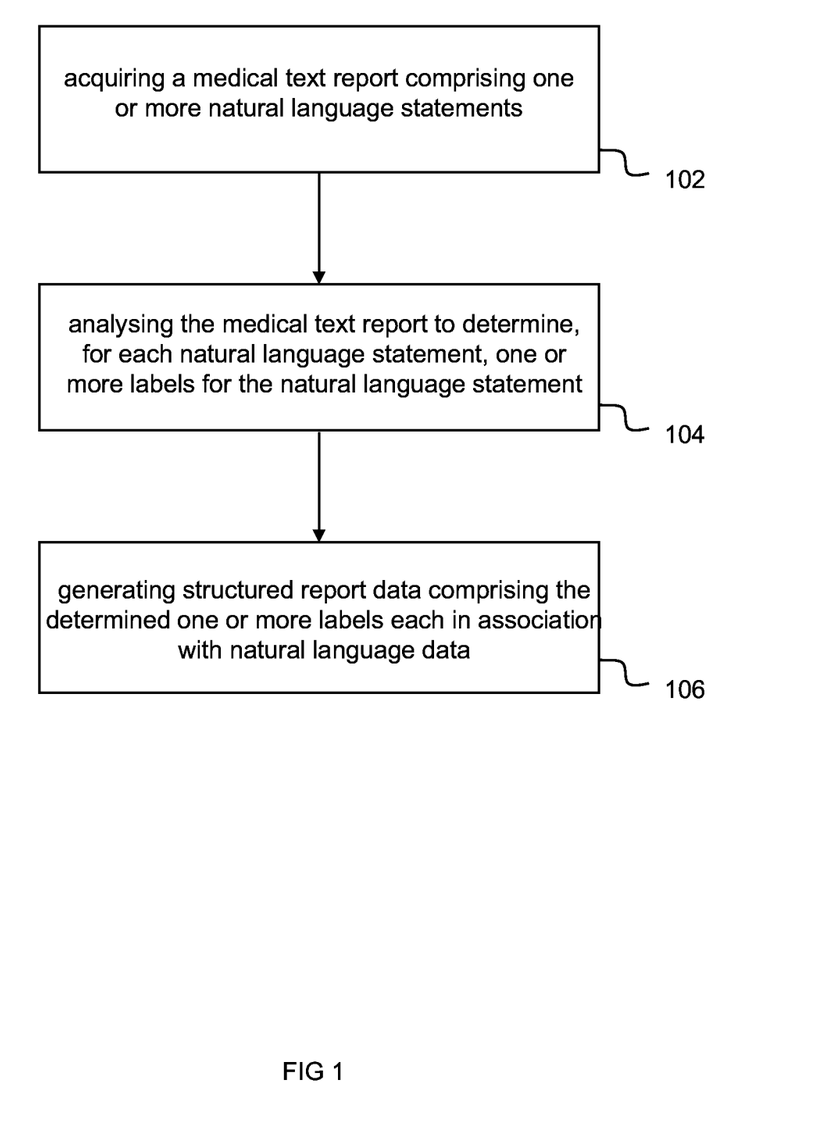
FIG. 1 illustrates schematically a flow diagram of a method according to an example.

FIG. 1 illustrates schematically a flow diagram of acts of a method of generating structured report data from a medical text report, according to an example.

Referring to FIG. 1, the method includes, in act 102, acquiring a medical text report including one or more natural language statements each including one or more words.

The medical text report may be a radiology report. For example, a radiographer may carry out medical imaging of a patient and a radiologist may read or interpret the resulting image or images and produce a text radiology report of their findings.

The medical imaging may include, for example, Computed Tomography (CT) scanning, for example Computed Tomography Angiography (CTA), or may include, for example, Magnetic Resonance Imaging (MRI), for example stress perfusion cardiac MRI.

Figure 2:
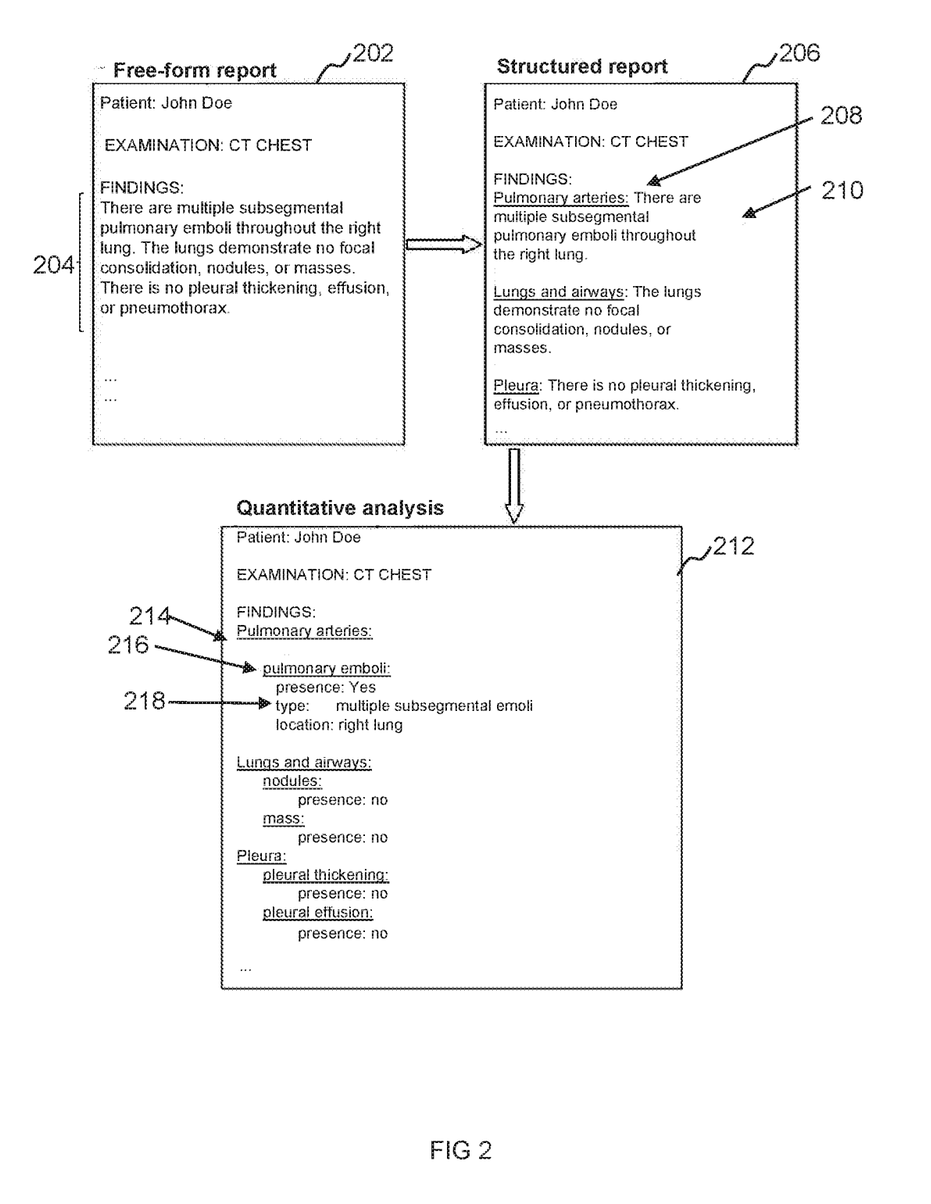
FIG. 2 illustrates schematically a medical text report and structured reports according to examples.

The radiology report may include text entered by the radiologist or other user directly into a computer via a keyboard or the like, or dictated by the radiologist, and voice-to-text software of the computer may be used to convert the dictated words into text, for example. An example medical text report 202 is illustrated in FIG. 2. The medical text report 202 is a radiology report 202. The medical text report 202 includes natural language statements 204 (three are shown in FIG. 2).

The medical text report includes one or more natural language statements. A natural language statement may be, for example, a sentence in a natural language, for example English. One or more of the natural language statements may be sentences. For example, a natural language statement of the example medical text report 202 of FIG. 2 is "There are multiple subsegmental pulmonary emboli throughout the right lung."

The natural language statements may include a medical finding of the radiologist. A medical finding may be defined as an observation made of the patient by a doctor (e.g. the radiologist), for example as a result of examination, imaging, or other test of the patient (e.g. radiography). For example, a medical finding of a radiologist may be a clinically significant observation made about the patient, for example a particular disease state or other medical feature of the patient, based on medical imaging of the patient or other examinations. For example, a medical finding may include, the presence or absence, type, location and/or a severity of the disease state, clinical abnormalities or other medical feature of the patient as surveyed by the radiologist. For example, a medical finding of the natural language statement "There are multiple subsegmental pulmonary emboli throughout the right lung." may be the presence of pulmonary emboli, and/or that the type of pulmonary emboli is subsegmental and/or the location of the pulmonary emboli is the right lung.

Acquiring the medical text report may include acquiring a completed medical text report. For example, a radiologist may complete the medical text report, and the medical text report may be stored electronically in a suitable storage. The medical text report may be stored as a text file, such that text of the report is computer readable. Acquiring the medical text report may include acquiring the medical text report, for example the text file, from the storage. Acquiring the medical text report may include receiving the medical text report over a communications network, for example from a database.

In some examples, one or more medical text reports may be acquired from a database or pre-existing medical text reports. For example, the database may be an Electronic Medical Record (EMR) database, an Electronic Health Record (HER) database, a Radiology Information System (RIS) database, and/or another form of database.

In some examples, acquiring the medical text report may include acquiring the natural language statements of the medical text report statement-by-statement. For example, the natural language statements may be acquired as and/or when they are created. For example, acquiring the medical text report may include acquiring a first natural language statement of the medical text report when the first natural language statement has been produced and before a second natural language statement of the medical text report has been produced. As another example, a natural language statement may be acquired each time the radiologist enters a natural language statement of the report. As another example, a new sentence may be acquired from voice-to-text software each time a radiologist finishes a sentence when dictating the radiology report. In such a way, the natural language statements may be acquired and/or processed on-the-fly. This may allow for the structured report to be produced when the radiologist is interpreting and reading the scan images. This may allow for the structured report to be more quickly available, and/or may reduce pre-processing of medical text reports into sentences.

The method includes, in act 104, analysing, using a computer implemented text analysis process, the medical text report to determine, for each natural language statement, one or more labels for the natural language statement.

The computer implemented analysis process may include natural language processing. The text analysis process may include pre-processing of the text of the medical text report. The pre-processing may include splitting the text of the medical text report into natural language statements. The pre-processing may include segmenting each word of each natural language statement.

The computer implemented text analysis process of act 104 of the method includes determining, for each word of each natural language statement of the acquired medical text report, and using word embeddings, a vector representing the word.

Word embeddings may be described as mappings of individual words or phrases of a vocabulary onto real-valued vectors representative thereof in a vector space. Each vector may be dense distributed representation of the word in the vector space. Word-embeddings may be learned/generated to provide that words or phrases that have a similar meaning have a similar representation in vector space.

The word embeddings may be learned using machine learning techniques. The word embeddings may be learned/ generated for words of a vocabulary of a corpus of text. The word embeddings may be learned/generated using a training process applied on the corpus of text.

The training process may be implemented by a deep learning network, for example based on a neural network. For example, the training may be implemented using a Recurrent Neural Network (RNN) architecture, in which an internal memory may be used to process arbitrary sequences of inputs. For example, the training may be implemented using a Long Short-Term Memory (LSTM) based Recurrent Neural Network architecture, for example including one or more LSTM cells for remembering values over arbitrary time intervals, and/or for example including gated recurrent units (GRU). The training may be implemented using a convolutional neural network (CNN). Other suitable neural networks may be used.

Various models may be employed for the training process for learning/generating the word embeddings. For example, the word embeddings may be learned using a skip-gram model implemented on a neural network. The skip-gram model may learn word embeddings for words given the local usage context of the words, where the context is defined by a window of neighbouring words. This window is a configurable parameter of the model. The skip-gram model may learn the word embeddings by predicting words that surround a given word. For example, all words of a corpus of text may be used to build a vocabulary. The word embeddings may initially map each word onto a vector of a given dimensionality that is populated with randomly generated numbers. The skip-gram model may take a word of the vocabulary and, using the word embedding associated with that word, attempt to predict words that surround that word in a given window. The skip-gram model may then compare the predictions with words that actually surround that word in the corpus of text and adjust word embeddings accordingly on the basis thereof. This process may be recursively applied until accurate word embeddings are generated. Other suitable models for learning word embeddings may be applied. The vector mapped by the word embeddings may be dense, i.e. of relatively low dimension, for example as compared to sparse word representations. This may allow the computer implemented text analysis process to be implemented relatively efficiently.

In some examples, the word embeddings used in the computer implemented text analysis process to determine the vectors for the words of the natural language statements of the medical text report may be obtained from a suitable word embedding database (for example that has been built up based on a generic text corpus not necessarily associated with medical text reports).

In some examples, the word embeddings may be trained/ generated from a corpus of medical text reports, for example from a corpus of radiology reports. For example, a number of radiology reports may be pre-collected as a training dataset. Each report may be split into sentences and words, for example as described above. All words in the training dataset may be used to build up a vocabulary for the word embedding training model. The word embeddings may then be generated/learned from the training data set, for example using the training techniques described above. The vectors determined for the words of the natural language statement of the medical text report in the text analysis process may then be determined using the generated/learned word-embeddings. Building the vocabulary and learning the word embeddings based on medical text reports (e.g. radiology reports) may allow for more complete vocabulary and more accurate word embeddings to be provided for the analysis, and hence for more reliable vectors to be determined for each word of the acquired medical text report.

The computer implemented text analysis process of act 104 of the method includes determining, based on the determined one or more vectors, and using a text classification model, the one or more labels associated with the natural language statement.

The text classification model may be a model for determining a label for a natural language statement based on the vector representations of the words of the natural language statement. The text classification model may apply a function to the vectors from word-embeddings of words or phrases of the natural language statements of the medical text report to be analysed and determine based on an output of that function one or more labels associated with that natural language statement. For example, the function may map the vectors from word-embeddings for words or phrases of the natural language statements of the medical text report onto one or more labels. For example, the text classification model may encode the vectors of each word of a sentence into a vector representing the sentence, for example using a neural network, and the text classification model may map the vector representing the sentence onto one or more labels. The text classification model may be based on or implemented using a deep learning network, for example a neural network, for a Recurrent Neural Network (RNN) architecture, in which an internal memory may be used to process arbitrary sequences of inputs, for example a Long Short-Term Memory (LSTM) based Recurrent Neural Network architecture, for example including one or more LSTM cells for remembering values over arbitrary time intervals, and/or for example including gated recurrent units (GRU). The text classification model may be implemented using a convolutional neural network (CNN). The neural network may include an attention model, which may allow for the text classification model to attend to different parts (e.g. different words) of an input sentence differently. Other suitable neural networks may be used.

In some examples, the text classification model may classify which of a plurality of predefined labels a given natural language statement corresponds. For example, the text classification model may determine for each of a plurality of predefined labels, an association parameter indicating a degree to which the natural language statement is associated with the pre-defined label. The one or more labels associated with the natural language statement may then be determined based on the determined association parameter.

For example, the plurality of predefined labels may be "Pulmonary arteries," "Lungs and Airways" and "Pleura," and the model may determine that the natural language statement "There are multiple subsegmental pulmonary emboli throughout the right lung" has a larger association parameter for the label "Pulmonary arteries" than for the labels "Lungs and Airways" or "Pleura," and hence the text classification model may determine that the label accordingly. In some examples, the text classification algorithm may be arranged such that any one of the plurality of predefined labels that has an association parameter with a given natural language statement higher than a predefined threshold may be determined as a label for that natural language statement.

In some examples, the text classification model may determine a first label for a given natural language statement and a second label for the given natural language statement. For example, the second label may be a sub-label determined from the natural language statement. The sub-label may be determined in substantially the same way as the labels described above. For example, a sub-label for the given natural language statement may be determined from a plurality of pre-defined sub-labels in substantially the same way as described above. The sub-label may be narrower than the label. For example, the determined sub-label may relate to the natural language statement in a different and/or more specific way than the label. In some examples, the second label may indicate a medical finding of the natural language statement, e.g. a medical finding of a predefined list of medical findings which according to the text classification model the natural language statement is most closely associated. For example, for the natural language statement "There are multiple subsegmental pulmonary emboli throughout the right lung" a first label may be determined as "Pulmonary arteries" and a second label may be determined as "pulmonary emboli."

The text classification model may be trained using a training process to determine appropriate labels for a given natural language statement. For example, the function may be trained to map the vectors from the word-embeddings for the words or phrases of a given natural language statement onto appropriate labels for that natural language statement.

The training process may be implemented using a deep learning network, for example based on a neural network, for example any one or more of the example neural networks described above.

The text classification model training process may include machine learning techniques.

In some examples, the training process may include supervised learning. The supervised learning may include inferring the function from annotated training data including training examples. For example, the training may be based on a database of natural language statements, each statement being annotated with a ground-truth corresponding to a label (i.e. a label to be given by the text analysis process). For example, the supervised learning may be based on a database of natural language statements of a corpus of medical text reports, each statement being annotated (for example by a radiologist or other physician) with a ground-truth corresponding to a said label. The statements may be from a plurality of radiology reports pre-collected as a training data set and corpus for the training process. Each statement of the training data may represent an input object and the corresponding ground-truth a supervisory signal, for the training process. The training process may analyse the training data to produce an inferred function, which may then be used for determining a label for a given input natural language statement of a medical text report to be analysed.

For example, the training process may include acquiring a plurality of medical text reports as training data (for example pre-existing relevant radiology reports), splitting the reports intro sentences, and segmenting the words of each sentence. Each sentence may be then manually annotated by a clinical expert using predefined standards. The annotated sentences are then used a training samples for the training process. For example, the training may include using vectors from word embeddings for each one of the words of given annotated sentences as an input object and using the corresponding label annotations of each sentence as a supervisory signal, for training the text classification model to produce the inferred function.

In some examples, the training process of the text classification model may be self-supervised. For example, the training data set may not include sentences annotated manually with corresponding label ground truths, but rather the ground truths may be determined from the training data set itself. For example, the training data set may include pre-collected structured medical text reports. The structured medical text reports may include one or more said labels each in association with a natural language statement to which the label corresponds. The ground-truth for each natural language statement used in the training process may include the label from the structured report. For example, the structured medical text reports may include natural language statements written under headings or given in named sections of the reports. The training process may therefore use the headings or names of the sections of the reports under which a given natural language statement as the ground truth label for that statement.

The word embeddings used in the text classification model training process may be the same as or different to the word embeddings used in the computer implemented text analysis process itself.

The word embeddings used in the text classification model training process may be obtained from a suitable word embedding database (for example that has been built up based on a generic text corpus not necessarily associated with medical text reports) or may be trained/generated from a corpus of medical text reports, for example from a corpus of radiology reports as described above.

The text classification model and the word embeddings may be trained together or separately. In some examples, the corpus of medical text reports used for the training of the text classification model may be the same as the corpus of medical text reports used for the training/generation of the word embeddings. For example, the vocabulary and/or the word embeddings may be trained/generated based on the same training data as that on which the text classification model is trained.

In some examples, the word embeddings may be trained together with the training of the text classification model. For example, the vocabulary and word embeddings may first be generated for a given training data set (e.g. corpus of medical text reports), and those generated word embeddings then used in the training of the text classification model based on the given training data set.

The method includes, in act 106, generating structured report data including the determined one or more labels each in association with natural language data. The natural language data includes the natural language statement or data derived from the natural language statement to which the label corresponds. For example, the structured report data may include a text string including the label and the natural language data to which the label corresponds. As another example, the generated structured report data may include a table including the label and natural language data to which the label corresponds in a common row of the table.

A first example of generated structured report data is shown in the first example structured report 206 illustrated in FIG. 2. The structured report data of the first example report 206 is generated from the medical text report 202. The generated structured report data of the first example structured report 206 includes determined labels 208 (three are shown) each in association with the natural language statement 210 to which the label corresponds. As one example, the natural language statement 210 "There are multiple subsegmental pulmonary emboli throughout the right lung" has the label 208 "Pulmonary arteries." A second example of generated structured report data is shown in the second example structured report 212 illustrated in FIG. 2. The structured report data of the second example structured report 212 includes determined labels 214, 216 (a total of eight are shown) each in association with data 218 derived from the natural language statement to which the label corresponds. As one example, the labels 214, 216 "Pulmonary arteries" and "pulmonary emboli" are presented in association with the data 218 "presence: yes; type: multiple subsegmental emboli; location: right lung" derived from the statement "There are multiple subsegmental pulmonary emboli throughout the right lung" of the medical text report 202.

The generated structured report data may be in a predetermined format, for example a predetermined field structure may be populated with the label and the associated natural language data. The generated structured data may be structured hierarchically. For example, the structured report data may be structured such that the one or more labels are in a first level of the hierarchical structure and the corresponding natural language data are in a second level of the hierarchical structure, the second level being lower than the first level in the hierarchical structure. For example, the generated structured report data may include the natural language data corresponding to a first natural language statement under a first heading or section or field including the label associated with the first natural language statement, and may include the natural language data corresponding to a second natural language statement under a second heading or section or field including the label associated with the second natural language statement. For example, as illustrated in FIG. 2, the structured report 206 includes structured report data including the first natural language statement "There are multiple subsegmental pulmonary emboli throughout the right lung" under the heading (i.e. label) "Pulmonary arteries," and a second natural language statement "The lungs demonstrate no focal consolidation, nodules or masses" under the heading (i.e. label) "Lungs and airways"

As mentioned above, in some examples, the natural language data includes the label and the natural language statement. For example, as per the first example structured report 206 of FIG. 2, the generated structured report data may include the label 208 "Pulmonary arteries," in association with the natural language statement 210 "There are multiple subsegmental pulmonary emboli throughout the right lung" to which the label corresponds.

In some examples the natural language data includes data derived from the natural language statement. In some examples, the data derived from the natural language statement may include one or more classifications of the natural language statement. The classifications may be with respect to a medical finding of the natural language statement. For example, the method (e.g. the computer implemented text analysis process described above) may include determining, using the text classification model, for each natural language statement, one or more classifications of the natural language statement with respect to a medical finding. Similarly to as described above for the labels, the model may determine one or more classifications with respect to a medical finding of a natural language statement by using an inferred function (learned or otherwise) that maps vectors from word embeddings of each word of the natural language statement onto one or more classifications with respect to one or more (for example predefined) medical findings. The determination of the classifications with respect to a medical finding may occur at the same time as the determination of the label.

The text classification model may be trained to determine an appropriate classification for a given natural language statement with respect to a medical finding similarly to as described above for the determination of the labels. Specifically, the text classification model may be trained based on machine learning techniques implemented on neural network-based architectures as described above. For example, the model may be trained using supervised learning based on a database of textual statements each annotated with a ground-truth corresponding to a classification with respect to first medical finding, or using self-supervised learning based on pre-collected medical text reports already structured to include classifications for a given natural language statement with respect to medical findings, which may be used as ground truths for the statement. As above, the training may include using vectors from word embeddings for each one of the words of given sentences as an input object and using the corresponding medical finding classification ground truths of each sentence as a supervisory signal, for training the text classification model to produce the inferred function. The word embeddings may be the same as those used above for determining the label.

The one or more classifications may include one or more of a presence classification, a type classification, and/or a location classification of the medical finding. For example, the text classification model may be trained or otherwise configured to classify a natural language statement as positive with respect to a medical finding if the model determines that the statement positively indicates the presence of the medical finding. For example, the text classification model may classify the statement "There are multiple subsegmental pulmonary emboli throughout the right lung" as positive with respect to the medical finding "pulmonary emboli," and hence determine the presence classification "yes" for the medical finding "pulmonary emboli" for that statement. Similarly, the text classification model may determine the type classification of the medical finding "pulmonary emboli" in this statement as "multiple subsegmental emboli," and the location classification of the medical finding "pulmonary emboli" in this statement as "right lung." For example, the second example structured report 212 of FIG. 2 (also referred to as "Quantitative Analysis" in the Figures) is based on generated structured report data including the determined labels 214, 216 specifically "Pulmonary arteries" and "pulmonary emboli," in association with data 218 derived from the natural language statement 210 to which the label corresponds. Specifically, the data derived from the natural language statement includes the determined classifications 218 of the natural language statement with respect to the medical finding "pulmonary emboli" (i.e. the sub-label 216), specifically "presence: yes// type: multiple subsegmental emboli// location: right lung."

Figure 3:
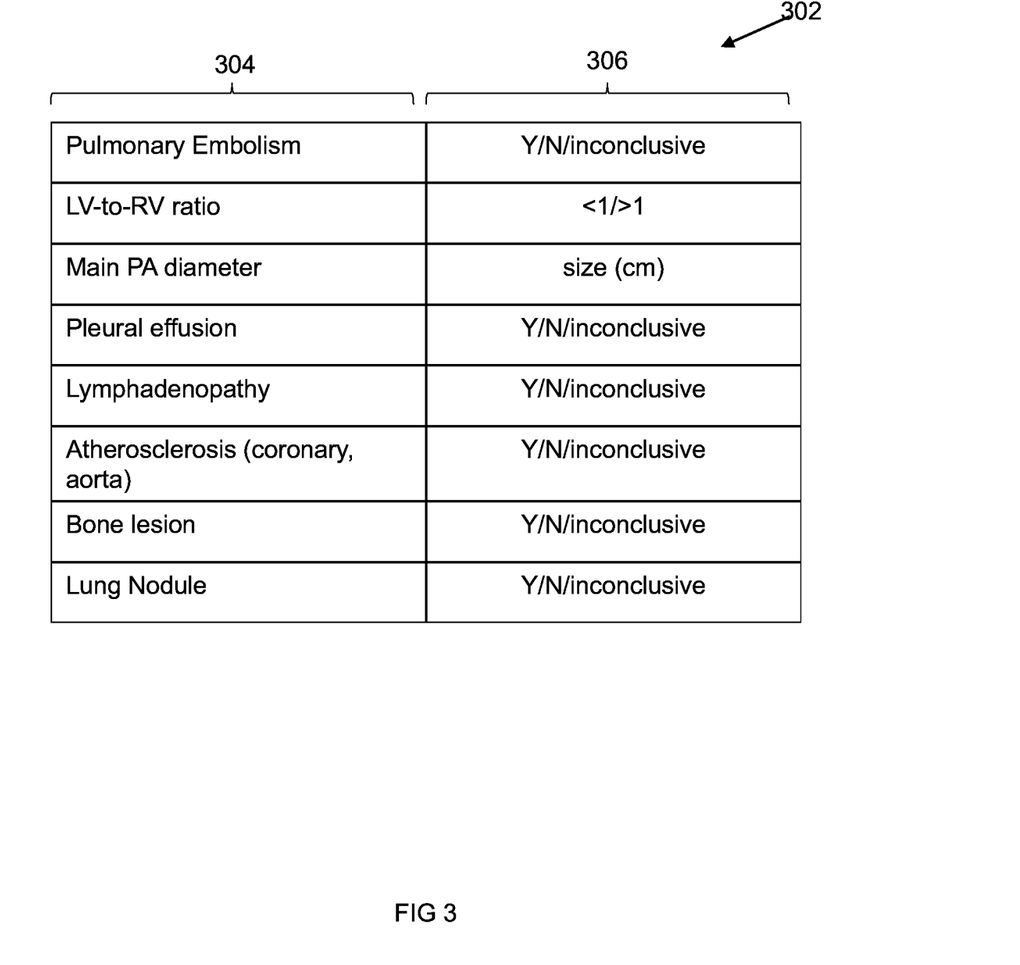
FIG. 3 illustrates schematically structured report data according to an example.

Other classifications of a given natural language statement with respect to a given medical finding may also be determined. For example, FIG. 3 illustrates schematically a table 302 representing example possible classifications that may be determined by the text classification model for a given natural language statement and hence which the data derived from a given natural statement may include. The left-hand column 304 lists medical findings and the right-hand column 306 lists classifications that may be made with respect to the medical findings. For example, for a given natural language statement, the classification with respect to "pulmonary embolism" may be determined as one of "Y/N/inconclusive" (i.e. Yes, it is present, or No it is not present, or the statement is Inconclusive with respect to its presence); with respect to "LV-to-RV ratio" (i.e. Left Ventricle-to-Right Ventricle diameter ratio, a parameter of pulmonary CTA) may be determined as one of "<1/>1" (less than 1 or greater than 1); with respect to "Main PA diameter" (i.e. main pulmonary artery diameter) may be determined as a size in centimetres; with respect to "Plural effusion" may be determined as one of "Y/N/inconclusive"; with respect to "Lymphadenopathy" may be determined as one of "Y/N/inconclusive"; with respect to Atherosclerosis (coronary, aorta" may be determined as one of "Y/N/inconclusive"; with respect to "Bone lesion" may be determined as one of "Y/N/inconclusive"; and/or with respect to "Lung Nodule" may be determined as one of "Y/N/inconclusive."

The data derived from a given natural language statement may itself be structured in a predetermined format, for example, a predetermined field structure may be populated with data derived from the natural language statement. For example, the data derived from a given natural language statement may be structured hierarchically, for example, to structure the output information by medical finding, or by one or more classifications with respect to one or more medical findings. For example, the data derived from a given natural language statement may include under a first heading or section or field classification data with respect to a first medical finding, and under a second heading or section or field classification data with respect to a second medical finding. For example, as per the second example structured report 212 of FIG. 2, the first heading or section or field of the data derived from the natural language statement may be "nodules" and under this heading or section or field may be the classification data related to nodules, for example "presence: no," and the second heading or section or field may be "mass" and under this heading or section of field may be the be the classification related to the "mass," e.g. "presence: no."

The structured report data may be output as a structured report, for example as a text file, or a printed report. The structured report data may be transmitted, for example over a suitable communications network, for example for receipt by one or more computers and/or suitable storage means. The generated structured report data may be stored, for example in a suitable database, for example as a suitably structured text file or another format.

The generated structured report data being structured so as to include the labels each in association with the respective natural language data may allow for a structured report to be generated where key information can be more readily identified and accessed, hence reducing the possibility of misdiagnosis based thereon. The structure of the structured report data may allow for the data to be efficiently transmitted using and/or stored in data model, which may allow for improved interoperability between systems accessing or sharing the data, and/or may allow for efficient searching of the data and/or comparisons between different records within the data model.

In some examples, as mentioned above, a structured report may be output based on the generated structured report data. As illustrated in FIG. 2, the output structured report 206, 212 may be structured such that the determined one or more labels 208, 214, 216 are each presented in association with the natural language data 210, 218 to which the label corresponds. As mentioned above, the first example structured report 206 of FIG. 2 includes structured report data generated from the medical text report 202. The structured report data in this example includes the determined label 208, specifically "Pulmonary arteries," in association with the natural language statement 210 to which the label corresponds, specifically "There are multiple subsegmental pulmonary emboli throughout the right lung." The label 206 is presented in association with the natural language statement 210. Specifically, the label 206 immediately precedes the natural language statement 210. The label is underlined, and acts as a heading for the natural language statement 210 in the report 206 to which the label corresponds. Each natural language statement is labelled in this way in the structured report 206.

The second example structured report 212 (also referred to as "Quantitative Analysis" in the Figures) includes structured report data generated from the medical text report 202. The second example structured report 212 presents the determined label 214, specifically "Pulmonary arteries," and the determined label 216, specifically "pulmonary emboli," in association with data 218 of the natural language statement to which the labels corresponds, specifically the classifications with respect to the first medical finding of pulmonary emboli: "presence: yes// type: multiple subsegmental emboli// location: right lung." The labels 214, 216 are presented in association with the data 218 derived from the natural language statement 210. Specifically, the label 216 is presented on a line that immediately precedes the data 218 derived from the natural language statement 210, and the label 214 is presented on a line that immediately precedes the label 216. The labels 214, 216 act as headings for the data 218 derived from the natural language statement 210.

The structure of the output reports 206, 208 may allow for key information to be more readily identified and accessed, for example by a referring physician, as compared to the medical text reports 202 on which they are based. This may allow for the structured reports to be easier to read, and hence may help prevent misdiagnosis based thereon, for example.

In some examples, the second example structured report 212 including the data derived from the natural language statements may be output directly based on the structured report data generated based on the medical text report 202. In some examples (as implied by the arrows illustrated in FIG. 2), the second example structured report 212 including the data derived from the natural language statements may be output based on the first example structured report 206, for example by determining the classifications with respect to medical findings as described above based on the natural language statements of the first example structured report 206.

In some examples, the generated structured report data may be stored in a database. Specifically, the method may include storing the generated structured report data in a structured database. The structured database may be structured so as to mirror the structure of the generated structured report data. For example, the structured database may be structured such that the determined one or more labels are each stored in association with the natural language data to which the label corresponds. For example, the database may include a table including a first column including labels and a second column including natural language data, and a given label and the natural language data to which the given label corresponds may be in a common row of the table. The database may include a predetermined field structure populated with the label and the associated natural language data, which may be structured hierarchically, for example such that the labels are in a first level of the hierarchical structure and the associated natural language data are in a second, lower, level of the hierarchical structure. Further, the database may be structured to provide that data derived from a given natural language statement is stored hierarchically, for example, structured by medical finding, for example as described above.

The generated structured report data being stored in a structured database as described above may allow for improved interoperability or data exchange between systems that may access or share the data and/or integration of data from sources of structured report data into one or more centralised locations, for example. Alternatively or additionally, this may allow for efficient searching of the data, for example in response to a given search query to be conducted. For example, a search for medical text reports relating to pulmonary arteries may be conducted among the labels, rather than a full text search of all the text of all the medical text reports.

In some examples, a search for natural language data may be performed or directed based at least in part on one or more labels of the database, for example via the labels of the database. For example, in examples where the database has a hierarchical structure described above, a search for medical text reports having a finding of "pulmonary emboli" being present may first include a search for records with the label "pulmonary arteries" followed by a search of the natural language data associated with that label, as opposed to a full text search of all of the text of all the medical text reports, or of all the text of all the natural language data. As another example, a search for medical text reports having a finding of "pulmonary emboli" being present may include a search for records with a medical finding sub-label of "pulmonary emboli." In examples where the labels include classifications with respect to medical findings, a search for medical text reports indicating a particular classification of a medical finding (e.g. presence, type, location) may be conducted among the classification fields, rather than a full text search of all the text of all the medical text reports. For example, a search for records indicating a finding of "pulmonary emboli" may be reduced to a search for records having a presence classification field indicating "Yes" with respect to the medical finding label "pulmonary emboli."

The generated structured report data being stored with such structure may also facilitate and/or improve the efficiency of comparison between records. For example, a single patient may undergo CTA a number of times at different points in time, resulting in a number of different radiology reports for the patient at different timepoints, which may each be analysed as described above to generate a plurality of sets of generated structured report data structured in the same way (i.e. according to a predefined format). This may allow for efficient comparison of report information, for example for a given patient, which may allow e.g. tracking of changes in report information over time. As another example, the structured report data may allow efficient comparison of the information in the radiology reports of two or more patients. For example, the structured report data may allow efficient identification and extraction of specific information for a specific group of patients, for example all patients that have a radiology report positively indicating the presence of a particular medical finding. As another example, a particular label or classification or field in the structured report data may be used to perform a cluster analysis (for example using a suitable data clustering algorithm), for example to group patients into clusters. A particular label or classification or field in the structured report data may also be used to sort patients, for example according to a severity of a certain condition. As another example, the structured report data, for example a particular label or classification or field in the structured report data, may be used to identify specific patients or groups of patients for a specific kind of follow-up medical examination and/or therapy.

The generated report data being stored with such structure may also provide for efficient text mining and/or interpretation, and/or for mining and/or interpretation of images of the medical text report which given natural language data is associated.

The method provides for structured report data to be generated from a medical text report. Such structured report data may allow for structured reports to be produced, which may allow for the key information contained therein to be more readily accessed. Such structured report data may allow for easier and/or more efficient updating, integration, and/or sharing of the information of the medical text reports across databases. Such structured report data may allow for further analysis, i.e. computer implemented analysis and/or searching, of the information of the medical text reports, to be performed more efficiently. Determining the labels using word embeddings may allow for the labels, and hence the structured report data, to be determined more efficiently and accurately, for example as compared to using natural language processing techniques based on grammatical rules.

Figure 4:
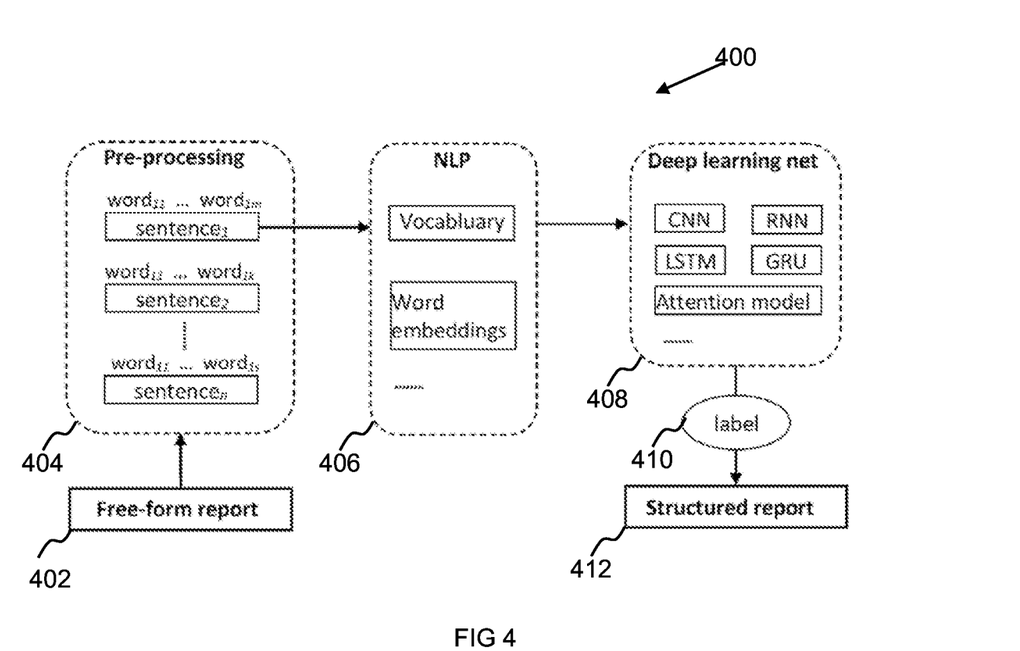
FIG. 4 illustrates schematically a diagram illustrating functional units according to an example.

FIG. 4 illustrates schematically an example arrangement 400 of functional units for implementing the method described above with reference to FIG. 1. The arrangement 400 includes a pre-processing unit 404, a natural language processing (NLP) unit 406, and a deep learning network 408. The pre-processing unit may implement act 102 of FIG. 1 and acquire or otherwise receive a medical text report 402 (also referred to a free-form report in the Figures). The pre-processing unit 404 may split the text of the medical text report 403 into n sentences (sentence$_1$, sentence$_2$ . . . sentence$_n$). The pre-processing unit 404 may segment each sentence into words (word$_{11}$ . . . word$_{1s}$). The NLP unit 406 may acquire each sentence (sentence$_1$, sentence$_2$ . . . sentence$_n$) including each segmented word (word$_{11}$ . . . word$_{1s}$) thereof, from the pre-processing unit 404, for example one at a time. The NLP 406 unit has stored therein or otherwise has access to the vocabulary and word embeddings according to any of the examples described above. The NLP unit 406 uses the vocabulary and the word-embeddings, for example as described above, to determine a vector representing each word of the given input sentence. The deep learning network 408 may include one or more neural networks as described above, e.g. one or more of a Recurrent Neural Network (RNN), a Long Short-Term Memory (LSTM) based Recurrent Neural Network, for example including gated recurrent units (GRU), for example including an attention model; a convolutional neural network (CNN). The text classification model may be implemented on the deep learning network 408. The deep learning network 408 determines, based on the determined one or more vectors, and using the text classification model, one or more labels 410 associated with the input sentence. For example, as described above, the text classification model may include a function that maps the vectors (from the word embeddings) representing the words of the input sentence onto a label 410 representing the sentence. For example, the text classification model may encode the vectors of each word into a vector representing the sentence, using a neural network, and this sentence vector may be used to determine the label 410. The text classification model may be trained for example as described above. The label 410 may then be used to generate a report 412 including the label 410 in association with natural language data including the natural language statement, or data derived from the natural language statement, as described above.

Figure 5:
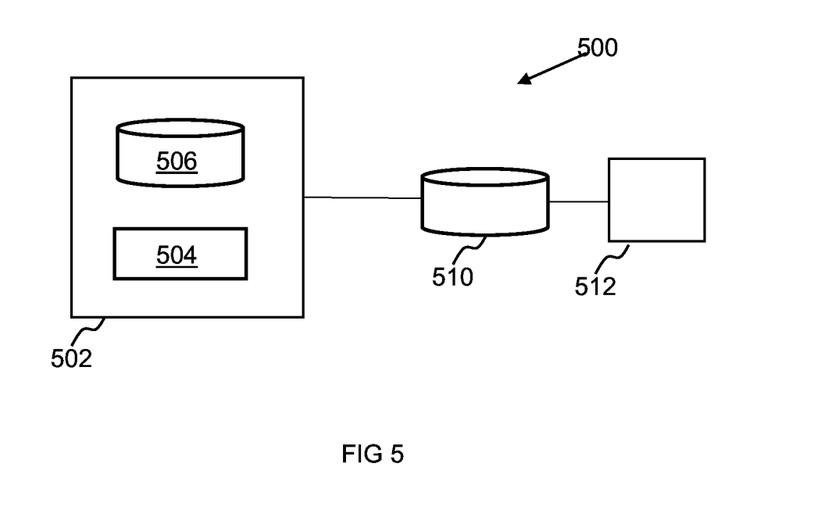
FIG. 5 illustrates schematically an apparatus according to an example.

FIG. 5 illustrates schematically a system 500, including an example apparatus 502, on which the method described above with reference to FIG. 1 may be performed, or on which the functional units described above with reference to FIG. 4, may be implemented. The apparatus 502 includes a processor 504 and a non-transitory memory 506. The memory 506 may store instructions, which when executed by the processor 504, cause the apparatus 502 to perform the method according to any one or combination of the examples described above with reference to FIG. 1, and/or to perform the functions of the functional units described above with reference to FIG. 4. For example, the apparatus 502 may be arranged to implement the pre-processing unit 404, the natural language processing unit 406 and/or the deep learning network 408 described above with reference to FIG. 4. The system 500 includes an external storage 510, for example a centralised database 510 such as a hospital or healthcare database. The apparatus 502 may be in communication with the external storage/database 510. In some examples, the apparatus 502 may be arranged to acquire medical text reports from the database 510 and/or store structured report data into the database 510. The memory 506 and/or the database 510 may be an example of a structured database as described above. The system 500 may include a further computer 512 or computers (one is shown in FIG. 5). The external storage 510 may be accessible by the further computer 512. The further computer 512 may for example extract structured report data from the database 510, and/or perform further processing on the structured report data, for example as described above.

The above described example methods and apparatus may provide for an artificial intelligence for radiology report analytics, that automatically converts unstructured findings of free-form radiology reports into structured and quantitative reports. As described above, in generating structured report data from medical text reports, the method and apparatus may allow for, for example, more efficient updating, integration, and/or sharing of information across databases and/or analysis, for example quantitative analysis in specific group of patients, or of a single patient, or for population health analytics, or cross-sectional analysis to identify high-risk patients and/or improve population health insights. Generating structured report data based on word embeddings enables automated generation of structured report data in an accurate and efficient manner, for example as compared to using natural language processing techniques based on grammatical rules. Further, using word embeddings allows the labels to be determined using the text classification model based on vectors (i.e. vectors of real numbers onto which the word embeddings map words of the natural language statement). This may allow the text analysis process to be particularly suited to computer implementation, as computers may perform computations based on vectors of real numbers more efficiently than based on text strings. For example, deep learning networks based on neural network architecture may process vectors more efficiently than strings of text.

The above examples are to be understood as illustrative examples. It is to be understood that any feature described in relation to any one example may be used alone, or in combination with other features described, and may also be used in combination with one or more features of any other of the examples, or any combination of any other of the examples. Furthermore, equivalents and modifications not described above may also be employed without departing from the scope of the invention, which is defined in the accompanying claims.

The invention claimed is:

1. A method of generating structured report data from a medical text report, the method comprising:
   acquiring a medical text report comprising multiple natural language statements each comprising one or more words;
   analysing, using a computer implemented text analysis, the medical text report, the analysing determining, for each natural language statement, one or more text labels for the natural language statement; and
   generating a structured report comprising text formed as structured report data comprising the determined one or more labels each in association with natural language data for each natural language statement, the natural language data comprising the natural language statement or data derived from the natural language statement to which the label corresponds;
   wherein the computer implemented text analysis comprises, for each natural language statement:
      determining, for each of the one or more words of the natural language statement and using word embeddings, a vector representing the word; and
      determining, based on the determined one or more of the vectors representing the words, and, using a text classification model, the one or more labels associated with the natural language statement.

2. The method according to claim 1, wherein the method further comprises storing the generated structured report data in a structured database such that the determined one or more labels are each stored in association with the natural language data to which the label corresponds.

3. The method according to claim 2, wherein the method further comprises performing a computer implemented searching process for said natural language data stored in the structured database based at least in part on said labels stored in the structured database.

4. The method according to claim 1, wherein the structured report data is structured such that the one or more labels are in a first level of a hierarchical structure and the corresponding natural language data are in a second level of the hierarchical structure, the second level being lower than the first level in the hierarchical structure.

5. The method according to claim 1, wherein the method further comprises outputting, based on the generated structured report data, the structured report structured such that the determined one or more labels are each presented in association with the natural language data to which the label corresponds.

6. The method according to claim 1, wherein the computer implemented text analysis process comprises, for each natural language statement:

determining, for each of a plurality of predefined labels, an association parameter indicating a degree to which the natural language statement is associated with the pre-defined label;

wherein the determining the one or more labels associated with the natural language statement is based on the determined association parameter.

7. The method according to claim 1, wherein the method comprises:

determining, using the text classification model, for each natural language statement, one or more classifications of the natural language statement with respect to a medical finding;

wherein, for each natural language statement, the natural langue data comprises the one or more classifications.

8. The method according to claim 1, wherein the acquiring the medical text report comprises acquiring a first of the natural language statements of the medical text report when the first natural language statement has been produced and before a second of the natural language statements of the medical text report has been produced.

9. The method according to claim 1, wherein the method further comprises training the text analysis process.

10. The method according to claim 9, wherein the training comprises training the text classification model based on a database of natural language statements of a plurality of further medical text reports, each statement being annotated with a ground-truth corresponding to a said label.

11. The method according to claim 10, wherein the plurality of further medical text reports are structured medical text reports comprising one or more said labels each in association with a natural language statement to which the label corresponds, and wherein the ground-truth for each natural language statement comprises the label.

12. The method according to claim 9, wherein the training comprises building a vocabulary and generating word embeddings from a plurality of further medical text reports or the plurality of further medical text reports, and wherein the determined one or more vectors are determined using the generated word-embeddings.

13. The method according to any one of claim 9, wherein the training is implemented using a neural network architecture.

14. An apparatus for generating structured report data from a medical text report, the apparatus comprising:

a memory storing a medical text report comprising one or more natural language statements each comprising one or more words; and a processor configured to:

analyse, using a computer implemented text analysis, the medical text report, the analysis determining, for each natural language statement, one or more labels for the natural language statement; and generate a structured report comprising text formed as structured report data comprising the determined one or more labels each in association with natural language data for each natural language statement, the natural language data comprising the natural language statement or data derived from the natural language statement to which the label corresponds;

wherein the computer implemented text analysis comprises, for each natural language statement:

a determination, for each of the one or more words of the natural language statement and, using word embeddings, of a vector representing the word; and a determination, based on the determined one or more of the vectors representing the words, and, using a text classification model, of the one or more labels associated with the natural language statement.

15. A non-transitory computer readable medium having stored therein instructions, which when executed on a computer, cause the computer to:

acquire a medical text report comprising one or more natural language statements each comprising one or more words;

analyse, using a computer implemented text analysis, the medical text report, the analysis determining, for each natural language statement, one or more labels for the natural language statement; and generate a structured report comprising text formed as structured report data comprising the determined one or more labels each in association with natural language data for each natural language statement, the natural language data comprising the natural language statement or data derived from the natural language statement to which the label corresponds;

wherein the computer implemented text analysis comprises, for each natural language statement:

a determination, for each of the one or more words of the natural language statement and using word embeddings, of a vector representing the word; and a determination, based on the determined one or more of the vectors representing the words, and, using a text classification model, of the one or more labels associated with the natural language statement.

* * * * *